(12) United States Patent
Aflatoon et al.

(10) Patent No.: US 9,204,973 B2
(45) Date of Patent: Dec. 8, 2015

(54) LATERALLY EXPANDABLE INTERBODY FUSION CAGE

(71) Applicants: Kamran Aflatoon, Cornoa del Mar, CA (US); Christopher W. Maurer, Irvine, CA (US)

(72) Inventors: Kamran Aflatoon, Cornoa del Mar, CA (US); Christopher W. Maurer, Irvine, CA (US)

( * ) Notice: Subject to any disclaimer, the term of this patent is extended or adjusted under 35 U.S.C. 154(b) by 278 days.

(21) Appl. No.: 13/892,724

(22) Filed: May 13, 2013

(65) Prior Publication Data

US 2013/0304213 A1    Nov. 14, 2013

Related U.S. Application Data

(60) Provisional application No. 61/645,662, filed on May 11, 2012.

(51) Int. Cl.
*A61F 2/44* (2006.01)
*A61F 2/28* (2006.01)
*A61F 2/30* (2006.01)

(52) U.S. Cl.
CPC .................. *A61F 2/4455* (2013.01); *A61F 2/44* (2013.01); *A61F 2/447* (2013.01); *A61F 2002/2835* (2013.01); *A61F 2002/30092* (2013.01); *A61F 2002/30166* (2013.01); *A61F 2002/30383* (2013.01); *A61F 2002/30428* (2013.01); *A61F 2002/30525* (2013.01); *A61F 2002/30571* (2013.01); *A61F 2002/30579* (2013.01)

(58) Field of Classification Search
CPC ............ A61F 2002/30092; A61F 2002/30166; A61F 2002/30383; A61F 2002/30428; A61F 2002/30579; A61F 2/44; A61F 2/4455; A61F 2/447
See application file for complete search history.

(56) References Cited

U.S. PATENT DOCUMENTS

| 5,026,373 | A | 6/1991 | Ray et al. |
| 5,989,290 | A | 11/1999 | Biedermann et al. |
| 6,241,769 | B1 | 6/2001 | Nicholson et al. |
| 8,257,443 | B2 | 9/2012 | Kamran et al. |
| 2010/0069912 | A1 * | 3/2010 | McCormack et al. .......... 606/90 |

FOREIGN PATENT DOCUMENTS

WO    WO 9814142 A1 *    4/1998   ................ A61F 2/44
WO    WO 2006134262 A1 *   12/2006   ................ A61F 2/44

* cited by examiner

*Primary Examiner* — Larry E Waggle, Jr.
(74) *Attorney, Agent, or Firm* — Ober, Kaler, Grimer & Shriver; Royal W. Craig

(57) ABSTRACT

An fusion cage having a longitudinal element and two planar bendable expansion arms slideably captured in a track on opposing sides, the expansion arms expandable from a pre-implantation position adjacent to the longitudinal element to a deployed position bounding an area around the longitudinal element in which bone graft material may be packed and retained after implantation into the intervertebral space. The longitudinal element is eliminated in favor of front and back lateral tracks in which the opposing ends of the expansion arms are slideably received so as to allow expansion of the bounded areas in both a lateral and anterior-posterior direction by sliding within the channels. Expansion of the area within the bendable members may be accomplished by rotation of leaves to which the bendable members are rigidly and slideably affixed.

10 Claims, 7 Drawing Sheets

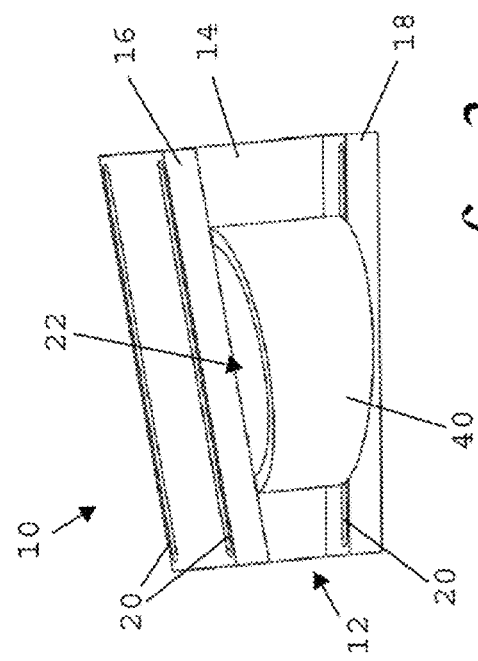
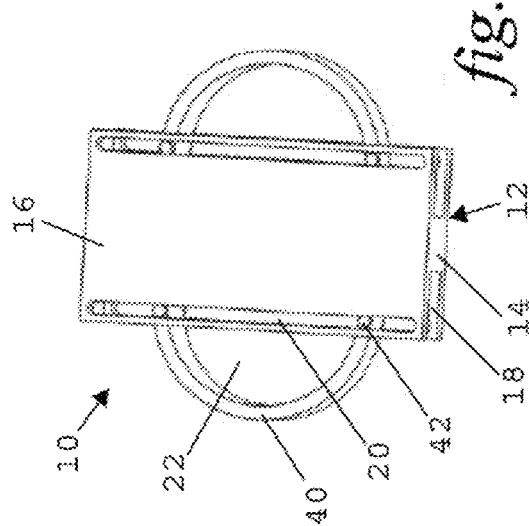
fig. 2
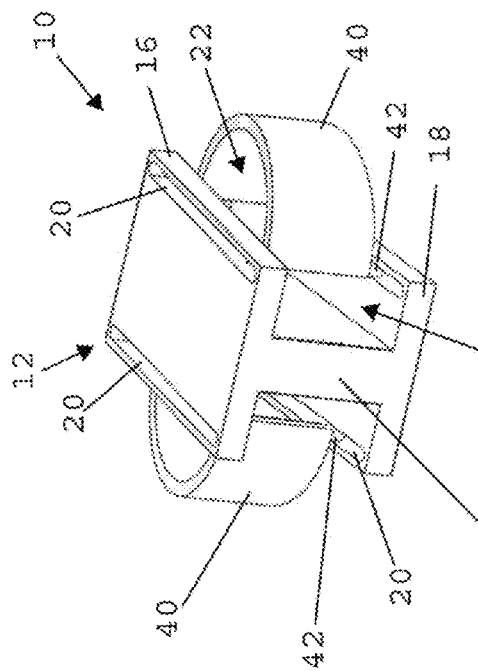
fig. 1
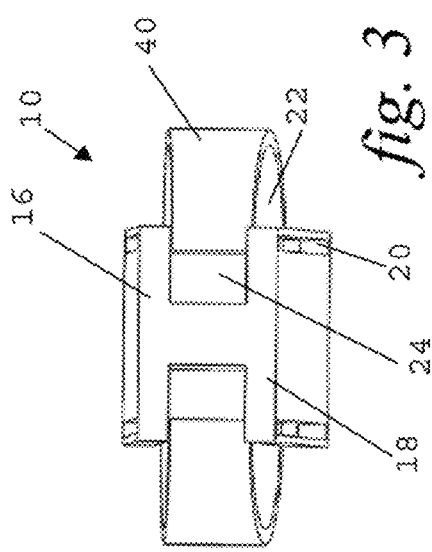
fig. 3
fig. 4

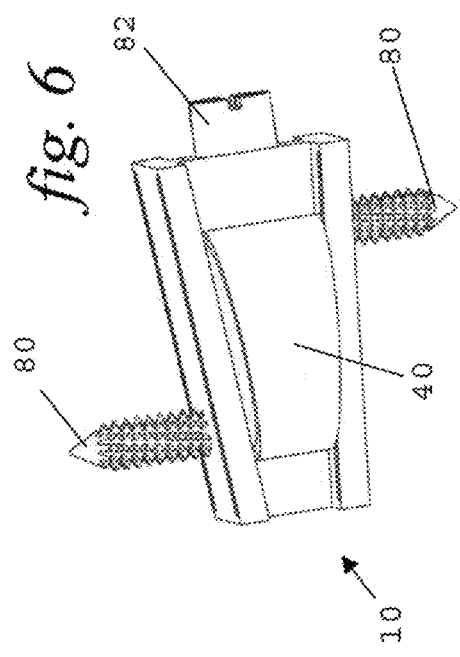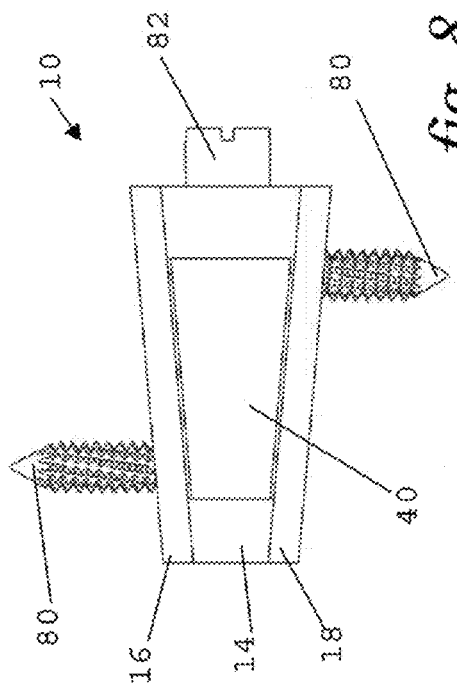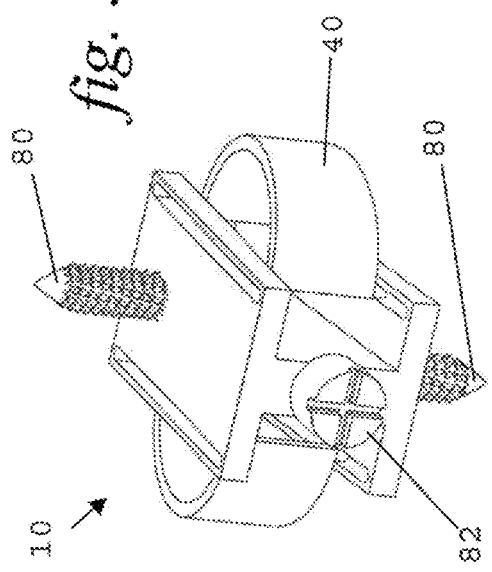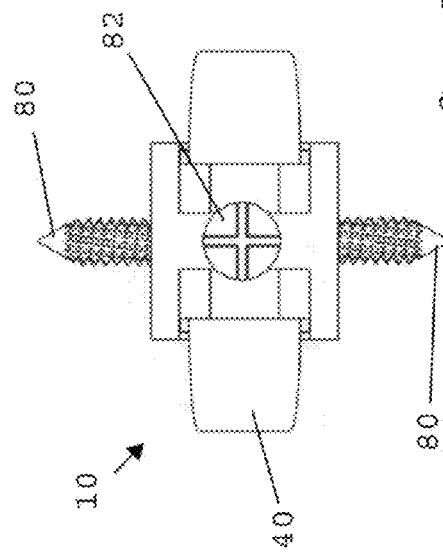

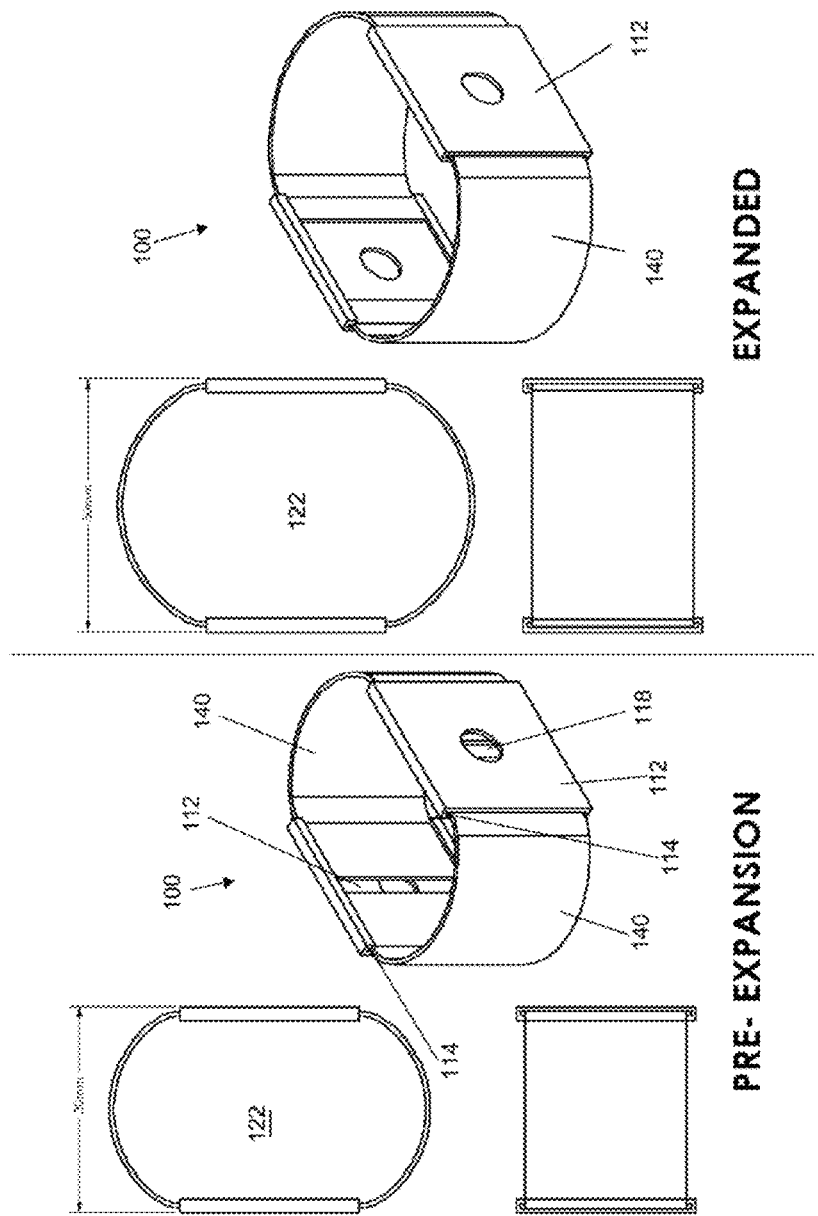

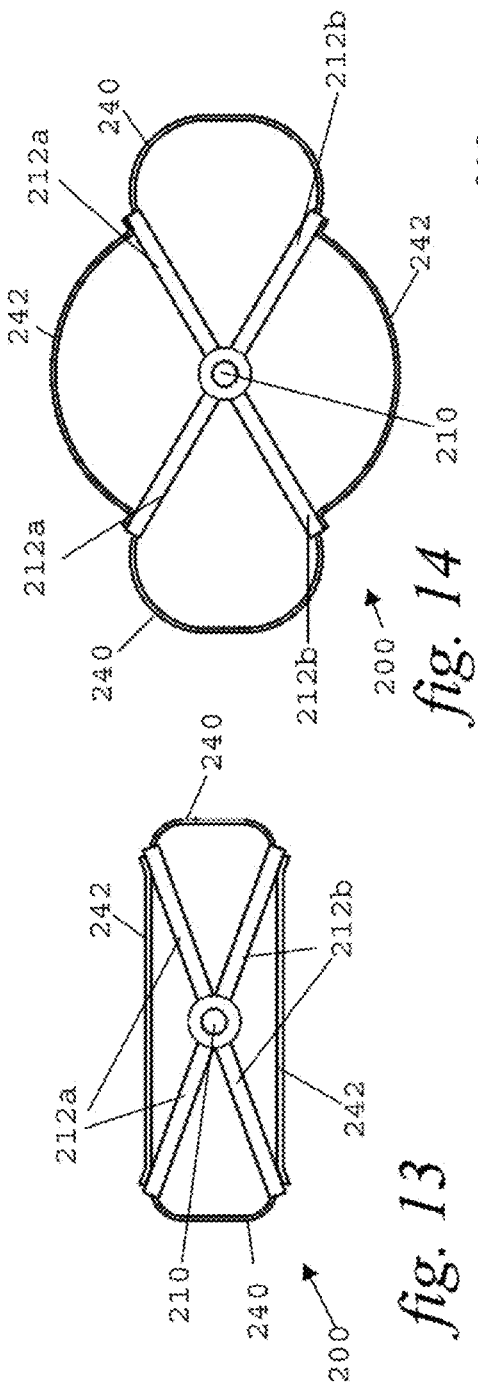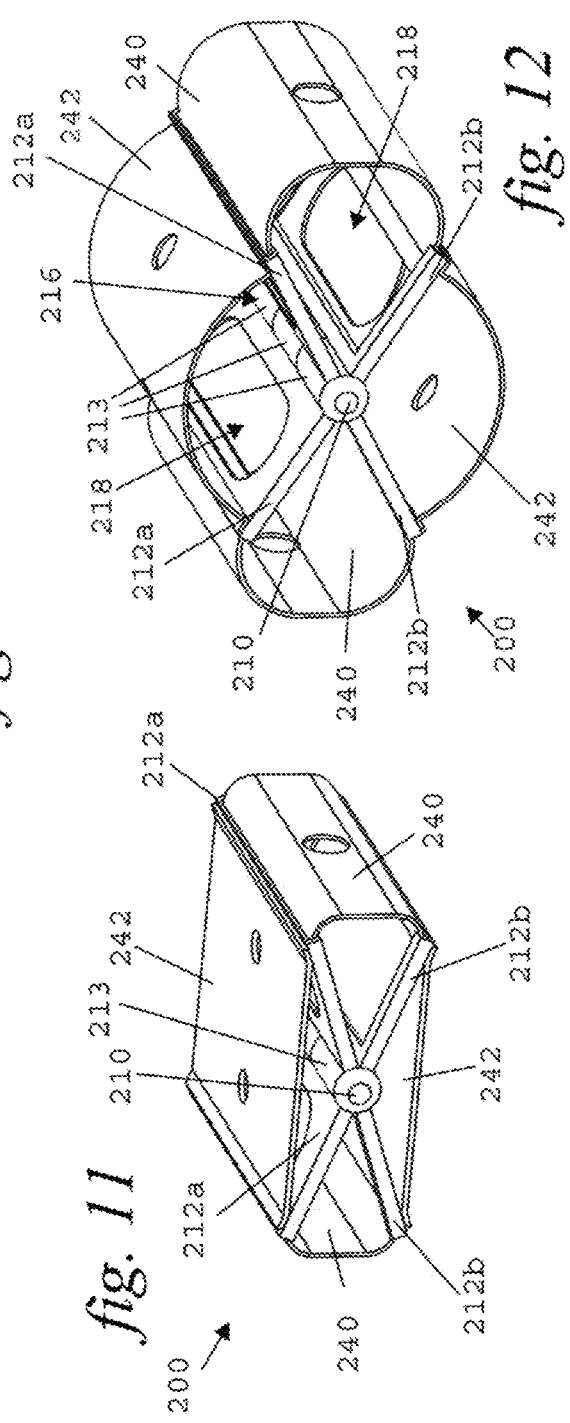

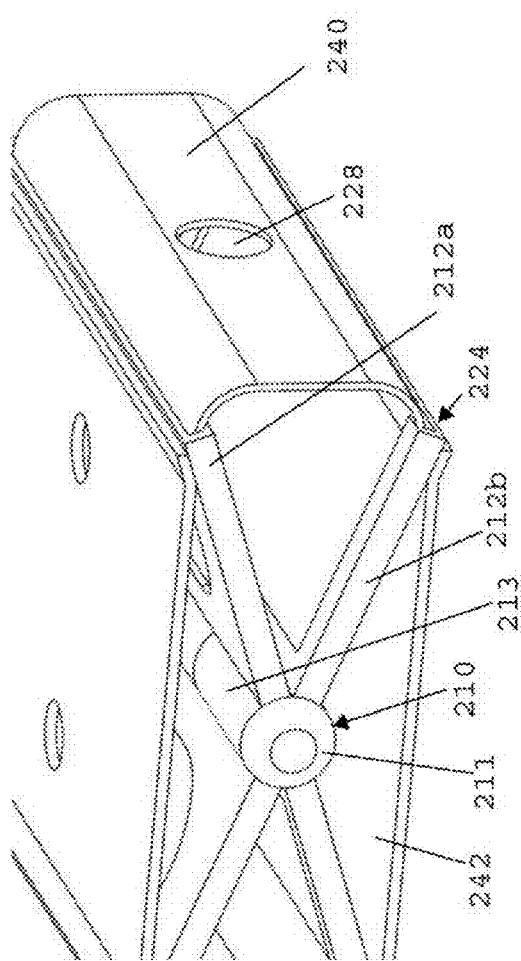
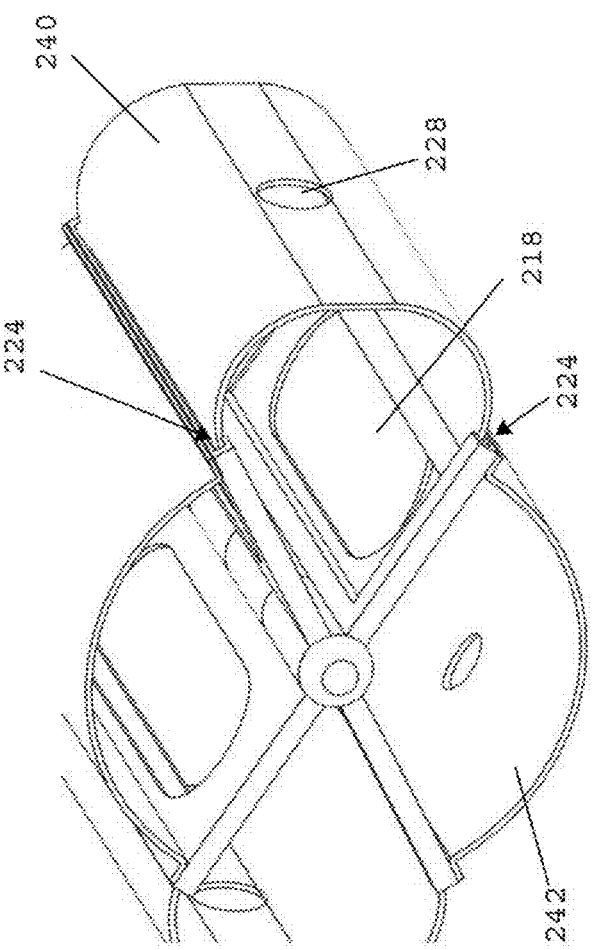

LATERALLY EXPANDABLE INTERBODY FUSION CAGE

CROSS-REFERENCE TO RELATED APPLICATION

This application claims the benefit under 35 U.S.C. §119 (e) of U.S. Provisional Patent Application Ser. No. 61/645,662 filed May 11, 2012, which is incorporated herein by reference.

BACKGROUND OF THE INVENTION

1. Field of the Invention

The present invention relates generally to devices and methods for treating spinal disorders and more specifically to an intervertebral device for aligning and maintaining the relative position of two or more adjacent vertebrae as well as to contain graft material to facilitate immobilization of the vertebra through fusion to eliminate the pain caused by abnormal motion.

2. Description of the Background

Degeneration of the intervertebral discs and the concomitant instability and translocation of the vertebra is a common cause of back pain and may result from a variety of problems including congenital deformity, age related degeneration, osteoporosis, tumor and disc herniation as a result of trauma. Disc degeneration, for whatever reason, results in compression of the spinal nerve roots resulting in pain. Palliative care is often successful in mild cases but more extreme or degenerative cases may require a surgical approach to stabilize the joint and relieve pressure.

A number of surgical approaches have been developed with varying degrees of success depending on the cause and severity of the damage. A ruptured disc impinging the nerve root may be partially excised to relieve pressure. In such a case the adjacent vertebra may be further fixated using rods, screws and plates in an attempt to stabilize the spine and delay or prevent further degeneration. Patients undergoing such excisions and fixations however, often require subsequent procedures to address recurrent pain. In many case such subsequent procedures include fusion. Spinal fusion, or spondylosyndesis, is a surgical technique used to combine two or more vertebrae utilizing supplementary bone graft tissue in conjunction with the body's natural osteoblastic processes to eliminate relative movement as a source of pain. A variety of approaches to fusion are available including posterior fusion, postero-lateral fusion and anterior or posterior interbody fusion.

In the more traditional posterior fusion approach, performed in conjunction with partial excision of the ruptured disc, growth is induced between the bony vertebral laminae to fix the position of the vertebra. In the postero-lateral fusion method bone growth is induced to join the transverse processes to prevent motion between the adjacent vertebrae. However, both posterior and postero-lateral fusion tend to cause bony overgrowth leading to nerve root compression and pain by spinal stenosis. This, coupled with other risks, limitations and disappointing fusion success rates have caused surgeons searching for alternate fusion means to develop interbody fusion techniques.

Interbody fusion techniques involve complete excision and replacement of the soft disc with autograft material harvested from the patient, prepared allograft from a donor source or, more recently, bone morphogenic protein. Most commonly performed in the lumbar region, the procedure can be accomplished from an anterior approach (Anterior Lumbar Interbody Fusion or ALIF) or a posterior approach (PLIF). In either case the procedure attempts to reconstruct the normal anatomic relationships between the bony and the neural structures and has many advantages. Specifically, weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

Successful fusion results in a contiguous growth of bone to create a solid mass that will unite the vertebra. When fusion graft material is first placed it is soft and movable and lacks cohesive strength and is therefore incapable of remaining in position or carrying any load without assistance. A variety of appliances have been developed that attempt to hold the vertebrae to be joined still relative to one another under normal spinal activity and daily stress in order to allow the fusion process to occur over the 18-24 month period generally required. Such appliances, often referred to as interbody cages, provide a mechanically rigid scaffold in which the graft material may be placed.

Cage designs vary widely but generally fall into three categories. Horizontal cylinders (1) are generally made from titanium and inserted by either the posterior or anterior approach into complimentary holes bored into the intervertebral space. They can be placed by open or minimally invasive techniques. U.S. Pat. No. 5,026,373 to Ray, et al. discloses a cage of this design that includes a perforated threaded exterior surface that can be screwed into place between the vertebra and packed with bone material. Bone growth through the perforations and into the cancelous bone of the vertebra exposed by the insertion results in the desired fusion.

A second design is in the form of a vertical cylinder or ring (2). Often referred to as a Harms cage, vertically cylindrical cages are also usually made from titanium and can be cut to length as desired so as to span larger segments of the lumbar spine. End caps are employed to prevent subsidence into the cancelous bone although this design suffers, as a result, from a requirement that its central void be packed with graft material prior to insertion. Due to its sharp edges it is most commonly inserted by open techniques. U.S. Pat. No. 5,989,290 to Biedermann et al, et al. discloses a cage of this design.

A third design form is the open box cage (3). Constructed of carbon, titanium or bio-compatible non-metallic materials, this design can be formed for an anatomical fit or to recreate the normal lumbar lordosis. Openings in the box walls permit graft material contained therein to contact the vertebral bone. Some designs utilize a single large cage. Alternately, a pair of smaller cages is utilized which can be inserted posteriorly using minimally invasive techniques. U.S. Pat. No. 6,241,769 to Nicolson et al, et al. discloses a box form cage having a central void having an open top and bottom and a dovetail system for structurally attaching the device to the adjacent vertebra which are prepared by cutting cooperative channels into their surfaces.

Cages provide enhanced mechanical stability prior to fusion, maintain the intervertebral disc height and ultimately provide a high rate of successful fusion. The ideal cage should rigidly immobilize the spine in all directions, be strong enough to withstand repeated loadings, have a modulus of elasticity similar to that of cortical bone. It should also be easy to insert by open or minimally invasive methods, resist subsidence, translation or retropulsion and be clinically effective. Cage designs further must balance the competing priorities of being small enough to be inserted through the incisions of minimally invasive techniques while also being large enough to fill a significant portion of the interbody space and present a significant area to the vertebral surface in which graft material can be inserted and retained to promote growth.

It would be therefore an improvement in this art to provide an interbody fusion cage for facilitating vertebral fusion and thereby eliminating spinal back pain caused by ruptured or degenerated vertebral discs which overcomes the deficiencies of prior known devices. Thus, it is an object of the present invention to provide an interbody fusion cage of open form design that can easily be placed in the evacuated interbody space to constrain relative vertebral motion and which can subsequently be secured again translation and retropulsion. It is a further object of the present invention to provide an interbody fusion cage that is sufficiently robust so as to withstand the forces imposed by normal daily activity on the part of the patient and which is clinically effective it retaining osteoconductive or osteoinductive material so as to facilitate fusion.

SUMMARY OF THE INVENTION

Accordingly, there is provided an interbody fusion cage having a longitudinal central element for insertion into the interbody space between adjacent vertebrae to promote fusion. A pair of upper and lower channels is longitudinally provided on either side of the central element forming. On each side, a track in which the ends of a generally planar spring-like or shape-memory expansion arm is slideably captured. Prior to implantation the expansion arms are collapsed against the sides of the central element so as to present a small cross section. After implantation the arms are released and their ends are allowed to slide within the channels such that the arms bend and expand outward to define a space in which bone graft material may be packed and retained to promote bone growth. In an alternate embodiment, one or more pins are rotatably extended from the upper and lower surfaces of the central element to engage the adjacent bone and secure the device in place. In yet another embodiment, the longitudinal central element is eliminated in favor of front and back lateral tracks in which the opposing ends of the expansion arms are slideably received. After insertion the expansion arms are allowed to slide along the tracks expanding the enclosed areas in both a lateral and anterior-posterior direction in order to maximize the contact area of bone graft material with the adjacent bone. Subsidence of the device compact the captured graft material to promote solid growth.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

BRIEF DESCRIPTION OF THE DRAWINGS

In the drawings:

FIG. 1 is a three-quarters perspective view of an embodiment according to the present invention from the front.

FIG. 2 is a side perspective view of an embodiment according to the present invention.

FIG. 3 is a perspective view of an embodiment according to the present invention from the back.

FIG. 4 is a perspective view of an embodiment according to the present invention from above.

FIG. 5 is a three-quarters perspective view of an alternate embodiment according to the present invention from the front.

FIG. 6 is a side perspective view of an alternate embodiment according to the present invention.

FIG. 7 is a front elevation view of an alternate embodiment according to the present invention from the back.

FIG. 8 is a side elevation view of an alternate embodiment according to the present invention from the back.

FIG. 9A is a composite view of yet another embodiment according to the present invention in the unexpanded state.

FIG. 9B is a composite view of the embodiment of FIG. 9A in the expanded state.

FIG. 11 is a perspective view of yet anther embodiment according to the present invention in a collapsed state.

FIG. 12 is a perspective view of the embodiment of FIG. 11 in an expanded state.

FIG. 13 is an elevation view of the embodiment of FIG. 11.

FIG. 14 is an elevation view of the embodiment of FIG. 12.

FIG. 16 is a partial detail view of the embodiment of FIGS. 11 and 12.

FIG. 17 is a partial detail view of the embodiment of FIGS. 11 and 12.

DETAILED DESCRIPTION OF THE PREFERRED EMBODIMENTS

Figure 10:
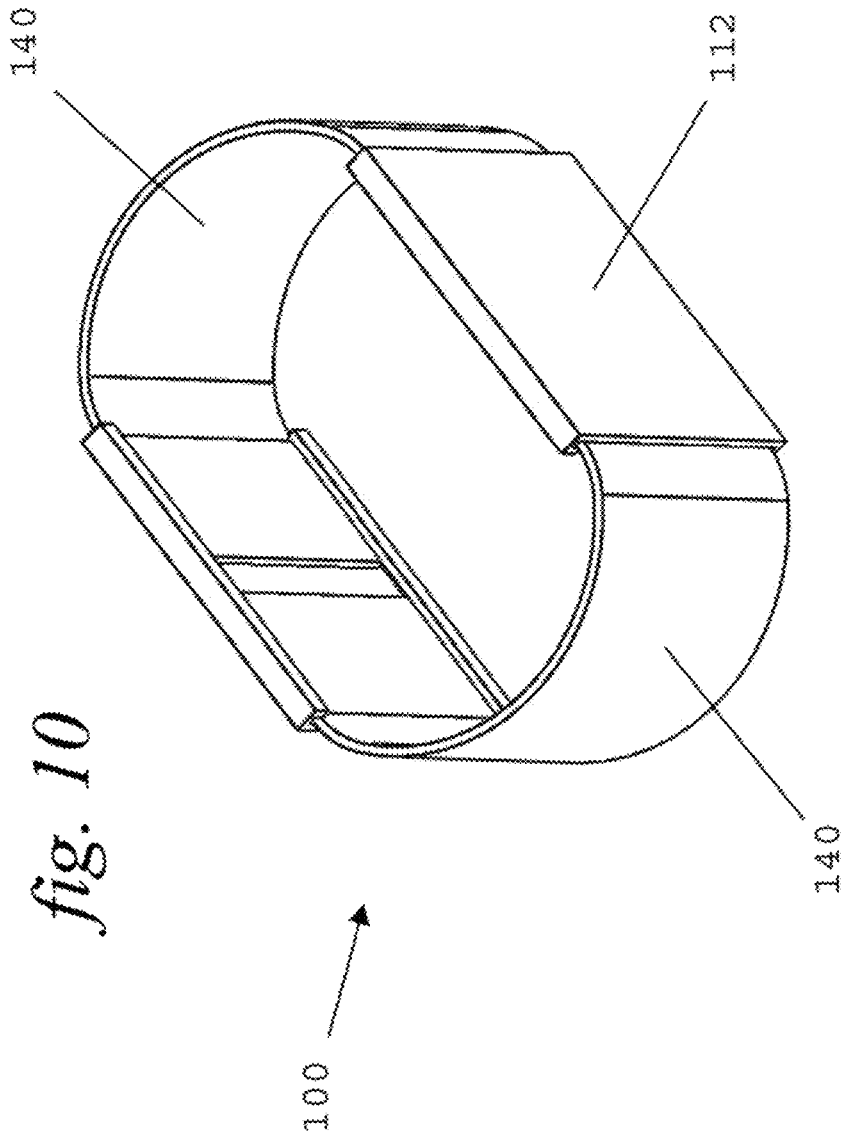
FIG. 10 is a perspective view of the embodiment of FIGS. 9A and 9B.
Figure 15:
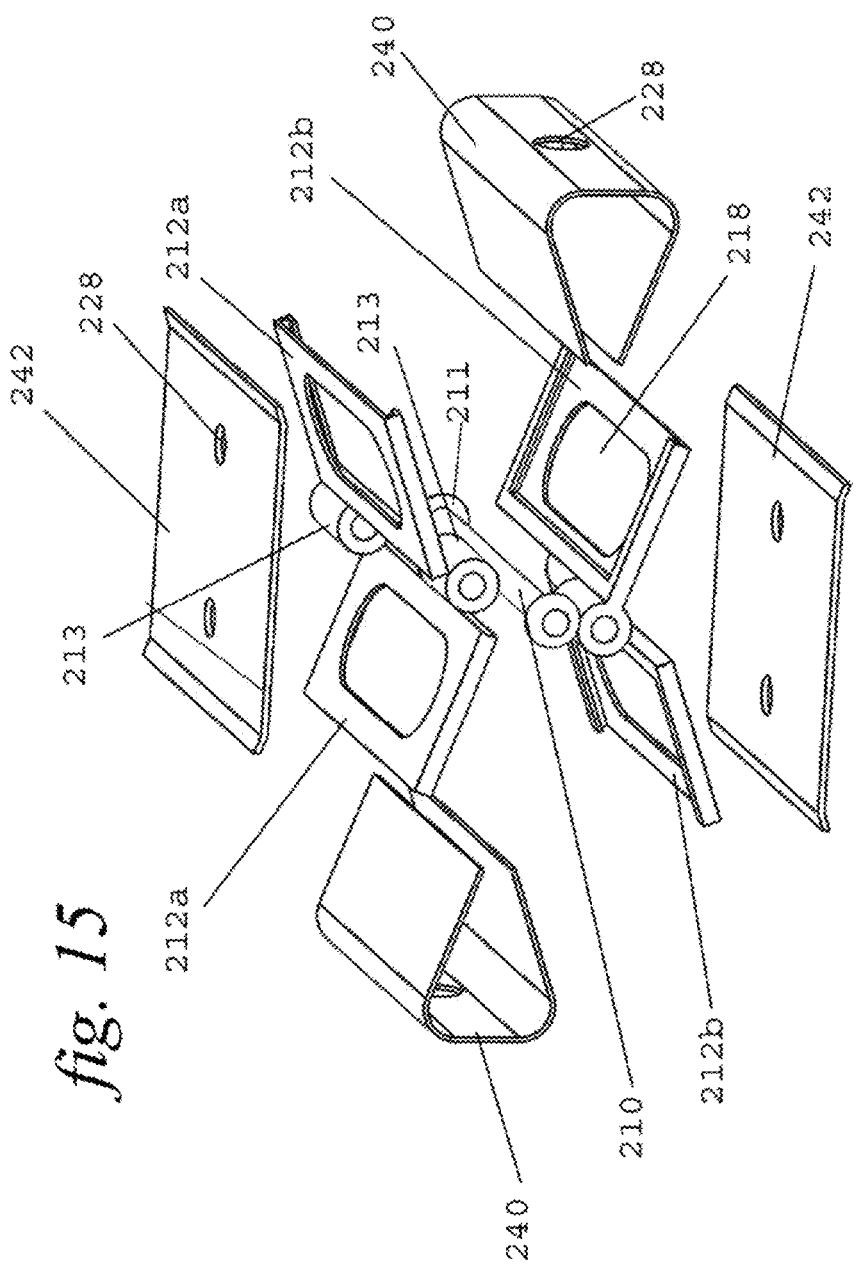
FIG. 15 is an exploded view of the embodiment of FIGS. 11 and 12.

With reference to FIGS. 1 through 4, an interbody fusion cage 10 according to the present invention includes a central element 12 preferably having an elongate shape and generally somewhat narrow or compact cross section to facilitate insertion of the cage 10 into the full or partially evacuated interbody space of the patient through minimally invasive means. Here, the central element 12 is provided with an "I" cross section having a central vertical element 14 for supporting the upper (superior) and lower (inferior) vertebra between which it is implanted, and a pair of opposing upper and lower lateral elements 16, 18 for engagement with the surfaces of the superior and inferior vertebra. In certain embodiments the upper and lower surfaces of the lateral elements 16, 18 may be textured such as for example with grooves, knurling or ridges for increased frictional engagement with the adjacent bone. Other means of securing the cage 10 in the interbody space may also be employed as will be discussed below.

The length of the central element 12 is preferably from 35 mm to 60 mm and is selected by the surgeon depending on the physiology of the particular patient in which it will be implanted. The height of the vertical element 14 is selected by the surgeon generally to replicate the natural height of the interbody space taking into account the thickness of the lateral elements 16, 18 and anticipated subsidence during fusion. With reference to FIG. 2, the height of the central element 12 may also be varied along its length to replicate the normal kyphotic or lordotic curvature of the spine. The lateral elements 16, 18 are typically coextensive with the central element 12 with respect to length. With respect to the width of the lateral elements 16, 18, the "I" shape of FIGS. 1-4 has been somewhat exaggerated for illustration purposes and the width of the lateral elements 16, 18 need only exceed that of the vertical element 14 by a sufficient width to accommodate upper and lower channels 20.

Longitudinal channels 20 are formed in cooperative pairs in the upper and lower surfaces of the lateral element 16, 18 in order to create a track in which an expansion arm is seated. The channels 20 are depicted as slots that extend through the lateral elements 16, 18 although this need not be so and the channels 20 may be provided in the form of grooves in the inside surfaces of the lateral elements 16, 18. Each channel 20 need not be a single, uninterrupted length as depicted but rather may be comprised of two or more partial channels as will be described. Within each pair of channels 20, an expansion arm 40 is slideably carried by a series of pins 42 extending from the edges of the arm 40 into the channels 20 as depicted in FIGS. 1-4. In certain embodiments the lateral elements 16, 18 may be omitted and the channels 20 formed directly in the opposing vertical faces of the vertical element 14 in which case the pins 42 will extend from the ends of the arm 40 into the channels 20 and be retained within the channels 20 by a ball end or similar enlargement slideably captured within the channel.

The expansion arms 40 are generally flat planar elements created from an elastically deformable material (i.e., spring-like) or, preferably, from a shape memory alloy such as Nitinol™. Although depicted in this application in their deployed state, the expansion arms 40 of the present cage 10 are generally stored in a flattened state such that the pins 42 are situated at the extremities of the channels 20 thereby providing a narrow total cross sectional area for ease of implantation by minimally invasive means. Once situated within the intervertebral space to the satisfaction of the surgeon, the expansion arms 40 are mechanically released (as by removal of an insertion tool) and deploy to the depicted state under the force of the stored spring energy or, preferably, by activation of the shape memory characteristics under the body heat of the patient. On deployment the pins 42 travel in the channels 20 in order to permit the expansion arms 40 to bow or bend outward and expand the lateral dimension of the cage.

Once in the deployed position the arms define additional areas 22 that are open to the adjacent superior and inferior vertebral surfaces and into which bone graft material may be inserted through, for example, an opening 24 to promote new bone growth and fusion. The depicted embodiment of the present invention provides both ends of the expansion arms 40 with pins 42 in the channels 20 such that on deployment, both ends of the expansion arms are permitted to move and the expansion area 22 is developed approximately in the middle of the cage along its length. In certain embodiments, one end of the expansion arm 40 may be permitted to rotate on pin 42 but not slide in the channel 20 such that the deployed arm 40 is situated at the front or back of the length of the cage. In certain other embodiments, the movement of an upper/lower pin 42 pair may be restricted within a channel by a stop which, on deployment, permits both ends of the expansion arm to slide in the channels 20 but limits the movement of one end in order to control the ultimate position of the areas 22 along the length of the cage 10.

The height of the expansion arms 40 is preferably at least equal to the height of the vertical element 14 (as depicted) and preferably equal to that of the central element 12 in which case they sit flush against the lateral faces of the upper and lower lateral elements 16, 18 prior to deployment. Some accommodation such as a notch is required in the expansion arms 40 to allow arms 40 to extend between the lateral members and permit the pins 42 to be received in the channels 20. It is preferable that the height of the expansion arms 40 equal that of the cage 10 such that the deployed expansion arms 40 engage the surfaces of the adjacent vertebra and contain any graft material inserted into the expansion area 22. The opening 24 at either end of the central element 12 may be capped off by insertion of a suitable closure element. In the case of the far end of the cage 10 which will be inaccessible after implantation, the vertical element 14 may be widened at a point equal to the deployed position of the back end of the expansion arm 40 to close off opening 24 at this end.

Where the overall height of the central element 12 is varied along its length to replicate the normal kyphotic or lordotic curvature of the spine, care must be taken when determining the height of the expansion arms 40 which also must be varied along their length according to the height of the cage at their final deployed position rather than their initial, stowed position. In such a scenario the length of the pins 42 and the depth of the channel 20 must be cooperatively selected to permit freedom of motion to the pins 42 while sliding in the channel 20 and also ensuring that the pins cannot leave the channel as they move along the channel during deployment and the distance between the upper and lower channels increases. In certain embodiments the pins 42 may be received within the expansion arms 42 and biased outward (up or down) by, for example, a spring in order to ensure the pins 42 remain in the channels 20 at all times.

With reference to FIGS. 5-8, an alternate embodiment of the present invention is depicted in which one or more pins 80 are deployable from the central element 12 in order to engage the adjacent bone and affix the cage in place. A pin deployment system, as described by U.S. patent application Ser. No. 12/660,153 filed Feb. 19, 2010 by the present inventors (now issued as U.S. Pat. No. 8,257,443) and incorporated herein by reference, is utilized to deploy the pins 80 by rotation of a worm drive screw 82 accessible on the front of the vertical element 14. The worm drive screw 82 is rotatably affixed within a channel longitudinally positioned with the vertical element 14. Vertical channels extending from the upper surface and or lower surfaces of the lateral elements 16, 18 partially intersect the longitudinal channel and house the pins 80. Each pin 80 is provided with a series of helically cut worm gear teeth on its external surface for engaging the worm drive screw assembly 82 where the channels intersect within each half. The pins 80 are simultaneously externally threaded and engaged to the cooperatively threaded internal surface of the longitudinal channel. After implantation between the adjacent vertebrae to be fused, the drive screw is turned by the surgeon using a tool to engage the screw head. Rotation of the worm drive screw in turn causes the pin(s) 80 to rotate with the longitudinal channel and advance through the upper or lower surfaces of the cage body and into the adjacent bone due to its threaded engagement with the channel wall. Multiple pins may be advanced by a single worm drive screw in order to stabilize the spine for fusion.

With reference to FIGS. 9A, 9B and 10, yet another interbody fusion cage 100 according to the present invention is depicted. The cage 100 is formed of front and back planar track elements 112 having a generally rectangular shape with a height selected to equal the interbody space between the vertebrae to be fused. The track elements 112 are preferably formed of a metal or polymer suitable for implantation such as stainless steel, peek, Delrin™, ultra-high molecular weight polyethylene or other implantable material having suitably low friction and high strength and stiffness characteristics. A hole 118 or other access means is preferably provided in one or both planar track elements to facilitate packing of the enclosed space 122 with bone graft material. Hole 118 is closeable as by a plug or other cooperative element. The upper and lower edges of the track element 112 are turned in and over to form opposing upper and lower channels 114 in which lateral expansion arms 140 are slideably received.

The expansion arms 140 are generally planar elements created, preferably, from a shape memory alloy such as Nitinol™ or an elastically deformable metal. In the pre expansion state depicted in FIG. 9A, the ends of the expansion arms 140 are fully received within the channels 114 of the track element 112 such that the ends of the arms 140 meet (or overlap) at the center of the track element partially or fully closing off hole 118. In this configuration the area 122 enclosed by the cage 100 is at its minimum and the anterior-posterior dimension of the cage is approximately 30 mm in the exemplary embodiment. Once inserted into the interbody space through a small incision the cage 100 is mechanically released and the shape memory characteristic of the expansion arms 140 is activated by the body heat of the patient causing the expansion arms to be drawn out of the planar track element by sliding in the channels 114. As a result the anterior-posterior dimension is increased to approximately 50 mm (in the exemplary embodiment), while the lateral dimension is also increased and the enclosed area 122 is increased to a maximum. With the expansion arms 114 deployed, graft material may be packed into the enclosed area via the hole 118 in the planar track elements and the hole plugged. Because the cage 100 presents only a small surface area to the inferior and superior vertebral bodies, some subsidence of the device into the bone is anticipated and even desirable in as much as this compresses the enclosed graft material promoting bone growth and fusion. The upper and lower surfaces of the track elements may be enlarged to as to present an increased surface area on which the adjacent bone may bear to limit or control subsidence. Where the expansion arms are fabricated from a non-memory, elastically deformable material, manual assistance may be required to ensure expansion of the cage 100.

With reference to FIGS. 11 through 17, yet another embodiment of the present invention is disclosed. As seen in FIG. 11, which is a depiction of the present embodiment of the cage 200 in the collapsed condition, and in FIG. 12 which depicts the same embodiment in the expanded condition, a central element is provided in the form of a pin 210 to which a set of four leaves 212a, 212b are rotatably affixed. Leaves 212 are preferably planar elements and are provided as two sets of upper and lower leaves in which each upper leaf 212a is paired with a lower leaf 212b to form a track as will be further described below. It should be noted that relative terms of position such as "upper" and "lower" as used herein are made with reference to the embodiments of the invention as depicted in the accompanying figures and are not meant to be limiting. The relative position of any element of the invention may be altered during implantation and/or use and thus be different than as depicted. The central portion of each generally planar leaf 212 is preferably provided with one or more cut-outs or holes 218 to facilitate the distribution of natural or synthetic bone graft introduced as a slurry into the cage during implantation as will be described.

Each leaf 112 is provided with one or more knuckles 213 that encircle the pin 210 to retain the leaf while facilitating rotation about the pin. The pin 210 is provided with a fixed or removable stop 211 at each end to retain the knuckles 213 on the pin without impeding rotation. The knuckles 213 are cooperatively positioned on the edge of their respective leaves to cooperatively engage the pin 210 to form a single barrel 216 about its length. In certain embodiments, the upper leaf 212a and lower leaf 212b diagonally opposed to one another across the pin 210 may be joined into a single unit engaged to the pin 210 by shared knuckles 213

The opposing ends of each leaf 212 are turned over and inward to form a pair of groove elements or channels 224 that together comprise a track in which one end of an expansion arm 240 is slideably received. The opposing end of the expansion arm 240 is slideably received in the channels 224 of the track of the opposing leaf 212 of the upper/lower leaf pair 212a, 212b. The expansion arms 240 are generally planar, flexible and preferably shape memory elements that are further preferably formed of Nitinol™ or other elastically deformable material having similar material properties. An additional expansion element 242 is provided between the two upper leaves 212a and the two lower leaves 212b. Like the expansion arms 240, the expansions elements 242 are generally planar, flexible and preferably shape memory elements that are preferably formed of Nitinol™ or other elastically deformable material. The expansion elements 242 are rigidly affixed along opposing edges to the distal ends of the leaves 212a, 212b on the outside surfaces of the leaves (opposite the channels 224 that comprise the tracks) so as not to impede the sliding of the expansion arms 240 within the track.

Prior to implantation the cage 200 is maintained in the collapsed position of FIGS. 11 and 13 in which the cross sectional area is minimized by fully advancing the ends of the expansion arms 240 into the channels 224 of the tracks toward the barrel 216. In this configuration the pairs of upper and lower leaves 212a, 212b are rotated about the pin so as to be as close to one another as possible in order to minimize the profile of the cage. Deformation of the Nitinol expansion arms 240 will limit rotation. The cage 200 can then be implanted into the patient by minimally invasive means and inserted into the partially or fully evacuated interbody space between the vertebrae to be fused such that the pin 210 is generally perpendicular to the longitudinal axis of the spinal column. Once situated between the superior and inferior vertebra, the cage 200 is rotated so that the pin 210 is generally parallel to the longitudinal axis of the spine (i.e., craniocaudal) and positioned to the satisfaction of the surgeon.

With the cage 200 in proper position, the leaves 212 are rotated about the pin 210 such that the upper and lower leaves 212a, 212b of each pair are rotated in opposing directions away from one another. Rotation of the leaves can be effected by the shape memory effect of the Nitinol™ elements (if such material is in use) and/or the insertion of a tool through one or more holes 228 provided in the shape memory elements 240, 242. As the upper and lower leaves 212a, 212b of a leaf par are rotated, the expansion arms slide within the channels 224 to the position depicted in FIGS. 12 and 14 thereby increasing the area enclosed with the cage 200. Similarly, as rotation of the two upper leaves 212a brings them closer together, the upper expansion element 242, being fixed to the distal ends of the upper leaves, is caused to bend outward further increasing the enclosed area of the cage. A similar result occurs with the lower expansion element 242 as rotation of the two lower leaves 212b brings them closer together. After expansion, any distraction of the vertebrae is released and the area enclosed by the cage can be filled with a slurry of bone graft material via the holes 228 in the deformable elements 240, 242 to stimulate and facilitate bone growth by the patient to fuse the adjacent vertebra. The open ends of the enclosed area of the cage allow direct contact between the graft slurry and the superior and inferior vertebral bodies.

It should be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

We claim:

1. An interbody fusion cage for insertion between adjacent vertebra, comprising:
   a longitudinal member having an upper surface and a lower surface, said upper surface joined to said lower surface on a first side of said longitudinal member and on a second side of said longitudinal member,
   on each of said first side and said second side, a pair of opposing channels, each pair of channels cooperatively aligned to form a track,
   in each track, an expansion arm comprising a bendable planar member and a plurality of pins slideably engaged in said opposing channels, said bendable member moveable from a flat position adjacent to said first or second side of said longitudinal member to an arcuate position defining an area within said bendable member and said longitudinal member;
   whereby bone graft material insertable into said defined area is configured to be retained therein in contact with said adjacent vertebra.

2. The fusion cage of claim 1 wherein said longitudinal member further comprises an upper lateral element and a lower lateral element joined by a vertical element, the width of said upper and lower lateral elements being greater than the width of said vertical element.

3. The fusion cage of claim 2 wherein the height of said planar member is equal to the height of said longitudinal member.

4. The fusion cage of claim 2 wherein the height of said planar member is equal to the height of said vertical element.

5. The fusion cage of claim 2 where said longitudinal member is "I" shaped in cross section.

6. The fusion cage of claim 2,
   wherein said upper lateral element comprises on one side said upper surface and on another side a first inside surface;
   wherein said lower lateral element comprises on one side said lower surface and on another side a second inside surface; and
   wherein said vertical element extends from said first inside surface to said second inside surface.

7. The fusion cage of claim 6 wherein a first channel of each said opposing pair of channels is formed in said first inside surface and a second channel of each said opposing pair of channels is formed in said second inside surface.

8. The fusion cage of claim 1 wherein the height of said longitudinal member varies along the length of said longitudinal member.

9. The fusion cage of claim 8 wherein the height of said planar member varies along the length of said planar member in cooperation with the height of said longitudinal member.

10. The fusion cage of claim 1 wherein said expansion arms are made from a shape memory alloy.

* * * * *